(12) United States Patent
Liska et al.

(10) Patent No.: US 6,811,542 B2
(45) Date of Patent: Nov. 2, 2004

(54) MICRODIALYSIS PROBE AND CATHETER ARRANGEMENT

(76) Inventors: Jan Liska, Sibyllegatan 53, S-114 43, Stockholm (SE); Anders Franco-Cereceda, St. Eriksplan 10, 113 32, Stockholm (SE)

( * ) Notice: Subject to any disclaimer, the term of this patent is extended or adjusted under 35 U.S.C. 154(b) by 215 days.

(21) Appl. No.: 10/177,108

(22) Filed: Jun. 24, 2002

(65) Prior Publication Data

US 2003/0236454 A1 Dec. 25, 2003

(51) Int. Cl.$^7$ .............................................. A61M 1/00
(52) U.S. Cl. ............................................. 604/29; 604/43
(58) Field of Search ........................... 604/29, 43, 513, 604/167.07, 167.01, 167.02, 523

(56) References Cited

U.S. PATENT DOCUMENTS

| | | | |
|---|---|---|---|
| 4,265,249 A | * | 5/1981 | Schindler et al. ............ 604/523 |
| 4,694,832 A | | 9/1987 | Ungerstedt |
| 5,106,365 A | | 4/1992 | Hernandez |
| 5,372,582 A | * | 12/1994 | Skrabal et al. .......... 604/164.11 |
| 5,441,481 A | | 8/1995 | Mishra et al. |
| 6,264,627 B1 | * | 7/2001 | Liska et al. .................... 604/29 |
| 6,346,090 B1 | | 2/2002 | Liska et al. |

FOREIGN PATENT DOCUMENTS

DE  90 02 100.2 U1  8/1990

OTHER PUBLICATIONS

Huxtble, Federataion Proceedings, vol. 39, No. 9, pp. 2685–2690 (1980).
Kimose et al., Thorac. cardiovasc, Surgeon, vol. 41, pp. 93–100 (1993).
European Heart Journal, vol. 8, pp. 206–207 (1987).
Kanthan et al., Journal of Neuroscience Mehtods, vol. 60, pp. 151–155 (1995).
Jansson et al., Microdialyssi of Human Tissue in Vivo, pp. E–218–E220 (1988).
Maggs et al., Brain and Skeletal Muscle Microdialysis, vol. 40, pp. S75–S82 (1997).
Roshdahl et al., Acra Physiol. Scand., vol. 159, pp. 261–262 (1997).
Swedish Article, Stockholm I, Apr. 1995.
Hagberg et al., Journal of Cerebral Blood Flow and Metabolism, vol. 5, No. 3, pp. 413–419 (1985).

* cited by examiner

*Primary Examiner*—Anhtuan T. Nguyen
(74) *Attorney, Agent, or Firm*—Birch, Stewart, Kolasch & Birch, LLP

(57) ABSTRACT

A microdialysis probe and catheter arrangement includes a catheter carrying in a distal end thereof a probe to be inserted in the body of a living being. The catheter has an elongate catheter body including a first channel for supplying a first fluid and a second channel for returning said first fluid. The first and second channels extend internally along the catheter body from a proximal end thereof to the probe. The probe includes a microdialysis membrane defining a dialysis chamber communicating with the first and second channels. A third channel extends internally along the catheter body and communicates with the second channel to supply a second fluid to thereto, thereby to increase the flow rate therein.

12 Claims, 2 Drawing Sheets

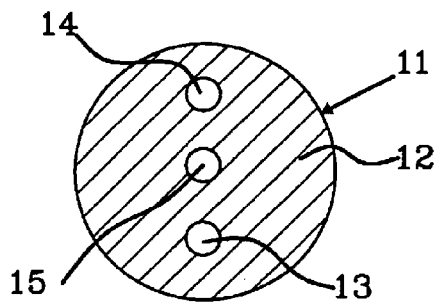
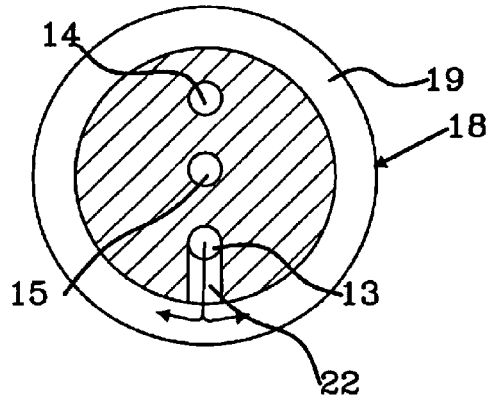
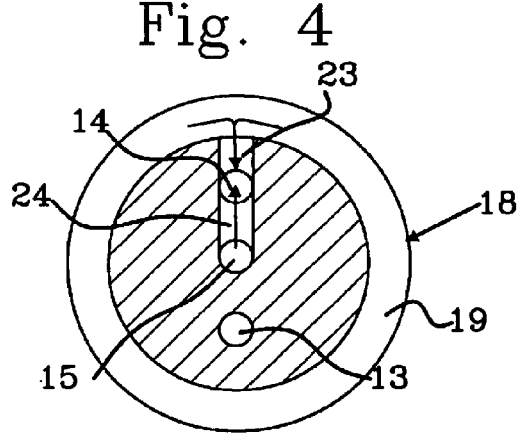
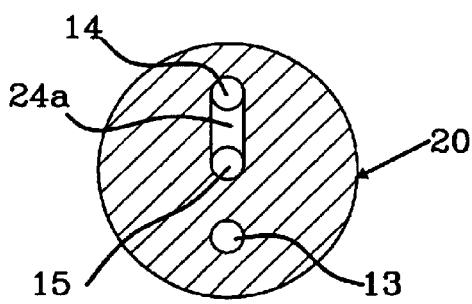
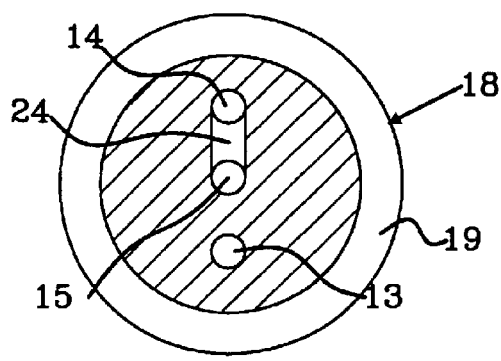
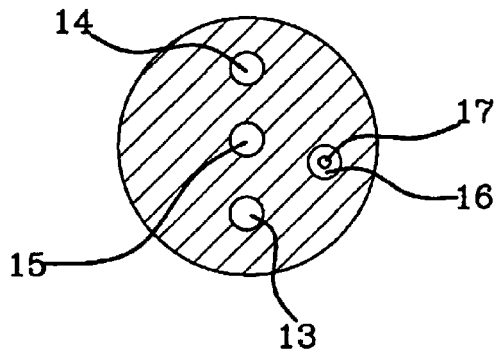

MICRODIALYSIS PROBE AND CATHETER ARRANGEMENT

FIELD OF THE INVENTION

The present invention concerns a microdialysis probe and catheter arrangement including a probe to be inserted in the body of a living being in order to perform various analyses.

BACKGROUND OF THE INVENTION

Microdialysis is used to monitor the interstitial fluid and blood in various body organs with respect to local metabolic changes. The technique involves sampling the chemistry of blood or body fluids of by analyzing the perfusate of a microdialysis probe inserted into a blood vessel, or, a tissue, respectively.

Microdialysis has been used both in experimental set-ups and in clinical situations, preferably for studies of brain metabolism. By introducing a microdialysis catheter into a blood vessel or a tissue, the content of the perfusate reflects the composition of the blood or the body fluid, respectively, over time due to the diffusion of substances back and forth over the dialysis membrane.

Relevant background art includes U.S. Pat. Nos. 4,694,832; 5,106,365; 6,264,627; and 6,346,090.

U.S. Pat. No. 4,694,832 to Ungerstedt discloses a dialysis probe comprising a dialysis membrane with associated ducts for achieving a perfusion fluid flow over the membrane. The single membrane is tubular and consists of a thin-walled permeable hose material referred to as a "hollow fiber" membrane. Ducts are provided for supplying and removing perfusion liquid to and from the interior of the membrane, and one of these ducts is disposed inside the hollow fiber membrane to extend to the distal end thereof. In order to protect and support the very thin membrane, the membrane is surrounded by a mounting, which is more rigid than the membrane and is preferably made as a thin-walled metal sleeve. The membrane is inserted in the mounting to be as close as possible to the wall of the sleeve. The wall of the sleeve has an opening in which a portion of the membrane surface is exposed.

U.S. Pat. No. 5,106,365 discloses a microdialysis probe comprising an outer sleeve containing tubes for delivering and removing dialysis products. The dialysis membrane is directly fixed to the end edge of the outer sleeve by gluing.

U.S. Pat. No. 6,264,627 by the present inventors concerns a catheter comprising an elongate catheter body, having a distal end and a proximal end. An outer essentially cylindrical surface, limiting a wall structure, encloses at least two channels including a first and a second channel for microdialysis solution. Each channel has a proximal end and a distal end. The first and second channels are interconnected at a first distance from the distal end of the catheter body so that microdialysis solution can flow from one channel to the other. An opening is provided in the catheter body at a second distance from its distal end, and a microdialysis membrane is arranged to cover the opening. A space in the catheter body formed by a portion of the first channel in connection with the opening forms a microdialysis chamber, having at least a portion of the microdialysis membrane as a part of its walls. The proximal ends of the first and second channels are connectable to external means for circulating, monitoring and/or analyzing the dialysis solution.

U.S. Pat. No. 6,346,090, also by the present inventors, discloses a microdialysis catheter comprising an elongate catheter body having first channel means for delivery of dialysis liquid and second channel means for discharge of dialysis liquid. A portion of the catheter body has a reduced diameter forming a straight cylindrical portion. A relatively stiff supporting sleeve is arranged around the cylindrical portion. A plurality of tubular membrane members is arranged in close relation to one another in one layer about the outer circumference of the supporting sleeve. Each tubular membrane member has an inlet end and an outlet end embedded in annular blocks arranged about the cylindrical portion at a proximal and a distal end thereof, respectively. The blocks allow fluid communication between the first channel means and one of the inlet and outlet ends of the plurality of tubular membrane members, and allow fluid communication between the second channel means and the other of the inlet and outlet ends of the plurality of tubular membrane members.

In microdialysis, the recovery, i.e., the percentage of specific substances obtained in the perfusate as compared to the true value in the surrounding blood or tissue, depends on various factors. The most important factors are the size of the pores in the membrane, the number of pores, the area of dialysis membrane, the perfusate volume in the dialysis chamber and the perfusion rate. To obtain a maximum recovery of substances from the blood or body fluid, it is desirable that the membrane area is as large as possible and that the rate and volume of perfusate contained in the dialysis chamber are as low as possible.

However, in order to achieve an acceptable time lag of 10–15 minutes or less with a low perfusion rate and good recovery, the catheters can have only a limited length, and that is the situation today.

It would be desirable, however, to enable the use of longer catheters, but this is not practicable due to the resulting extended time lags.

It is a problem, thus, to combine a low flow rate in the dialysis chamber in order to obtain good samples with a short transportation time for the samples from the dialysis chamber to the proximal end of an outlet channel.

SUMMARY OF THE INVENTION

It is an object of the present invention to solve the problem of providing a catheter having a high flow rate as regards return flow from a dialysis chamber, while still maintaining a low flow rate in the dialysis chamber to enable a proper diffusion over the dialysis membrane.

According to the present invention there is provided a probe and catheter arrangement, said catheter comprising an elongate catheter body having at least three internal channels extending therealong, a first of said channels delivering dialysis liquid to a dialysis chamber and a second of said channels discharging dialysis liquid from said dialysis chamber, a third of said channels communicating with said second channel to deliver a second liquid to said second channel to increase the flow rate therein.

BRIEF DESCRIPTION OF THE DRAWINGS

Further scope of applicability of the present invention will become apparent from the detailed description given hereinafter. However, it should be understood that the detailed description and specific examples, while indicating preferred embodiments of the invention, are given by way of example only, since various changes and modifications within the spirit and scope of the invention will become apparent to those skilled in the art from this detailed description.

FIG. 2 is a cross section through the catheter taken along line II—II in FIG. 1;

FIG. 3 is a cross section through the catheter and the probe taken along line III—III in FIG. 1;

FIG. 4 is a cross section through the catheter and the probe taken along line IV—IV in FIG. 1 showing a preferred location of a cross channel;

FIG. 5 is a cross section through the catheter and the probe taken along line V—V in FIG. 1 showing an alternative location of a cross channel;

FIG. 6 is a cross section through the catheter and the probe taken along line VI—VI in FIG. 1 showing a further alternative location of a cross channel; and FIG. 7 is a cross section through a catheter having a different channel arrangement.

DETAILED DESCRIPTION OF PREFERRED EMBODIMENTS

Figure 1:
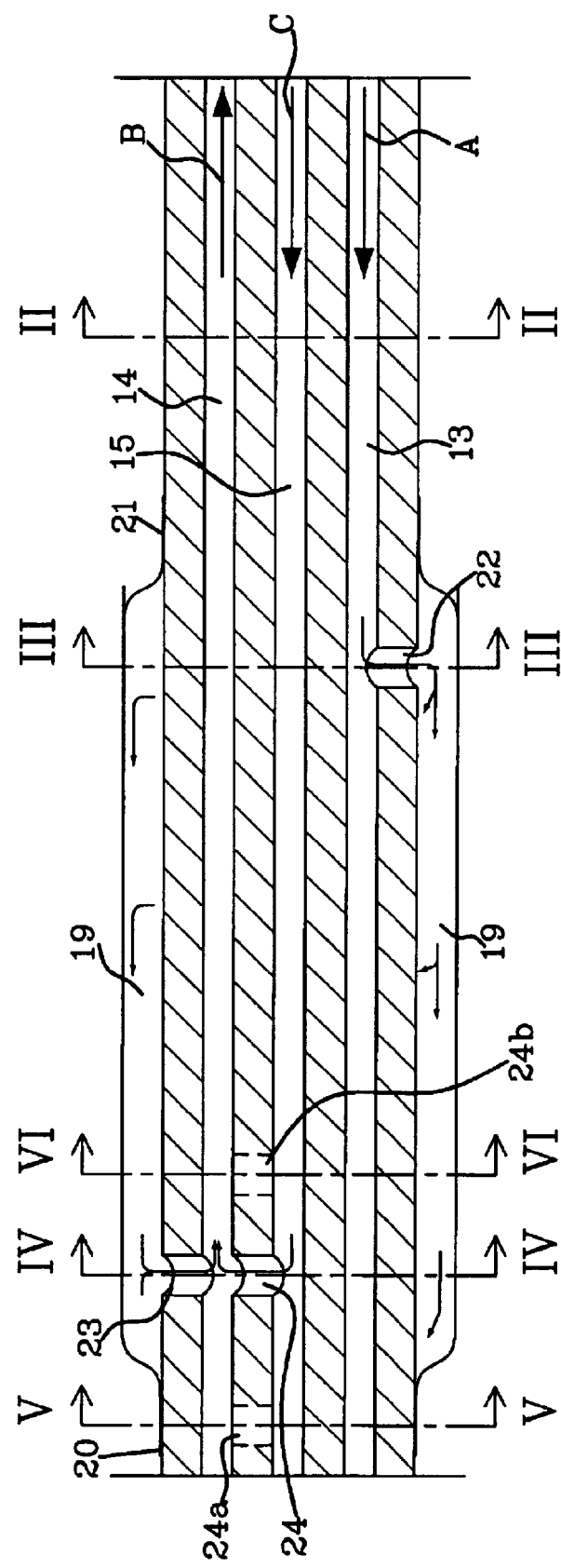
FIG. 1 is a longitudinal section through a microdialysis catheter and a probe arranged at a distal end thereof.

It should be understood that a microdialysis catheter according to the present invention may have a length of several meters and that FIG. 1 depicts only a very short portion thereof. It comprises a catheter body 12 formed preferably by extrusion of a suitable synthetic resin. Its diameter may be about 2 mm.

At least three liquid conducting channels 13, 14 and 15 extend along the length of the catheter body as shown in FIGS. 2–6.

Further channels may be provided as shown in FIG. 7, where a fourth channel 16 is provided to receive a guide wire 17 as known in the art.

The channels 13, 14 and 15 are shown here to be arranged along a common diametrical plane, although other channel patterns are possible. Preferably, the channels 13, 14 and 15 have equal, circular cross sections.

The first channel 13 is a supply channel for a first liquid, a dialysis or perfusion liquid, and its proximal end is connected to a non-shown source of such liquid. The second channel 14 is a return channel for dialysis liquid and its proximal end is connected to a non-shown apparatus for analyzing the liquid.

Close to the distal end of the catheter there is provided a tubular dialysis membrane 18 arranged around the catheter to form an annular dialysis chamber 19. The tubular membrane has a proximal end and a distal end, both being sealed against the outer surface of the catheter as shown at 20 and 21.

A first cross channel 22 is formed in the catheter body 12 to provide communication between the supply channel 13 and the dialysis chamber 19 close to its proximal end. A second cross channel 23 is formed in the catheter body to provide communication between the return channel 14 and the dialysis chamber 19 close to its distal end.

The distal ends of at least the channels 13 and 14 are sealed close to the distal end of the dialysis chamber in a non-shown manner, such as by plugging or heat sealing.

A microdialysis catheter and probe arrangement functions as follows: a microdialysis or perfusion liquid is introduced into the supply channel 13 (arrow A) to be brought therealong and through the first cross channel 22 out into the microdialysis chamber 19 where it will spread and move towards the distal end thereof. During its passage through the microdialysis chamber, the perfusion liquid mixes with and brings along substances from a body tissue or blood surrounding the probe and diffusing through the wall of the membrane. Eventually the perfusate escapes through the second cross channel 23 into the return channel 14 and is brought to the non-shown apparatus for analysis (arrow B).

Since the input or supply flow rate is set rather low in order to obtain a sufficient dwelling time for the perfusion liquid in the dialysis chamber, the return flow will have an equally low flow rate, provided, of course that the cross sectional areas of channels 13 and 14 are equal. As discussed above, particularly when thin catheters are involve, the return flow rate may be too low to obtain timely analysis results, for instance in the case of myocardial infarction, when it is crucial to promptly detect metabolic changes in the heart.

In order to increase the flow rate in the return channel, the present invention proposes to add a further flow to the return flow in the return channel. This is achieved by providing the third channel 15 which is fed from the proximate end of the catheter with a suitable second liquid (arrow C), preferably the same perfusion liquid as that running in channel 14, and by providing communication between the third channel 15 and the second channel 14 so as to add the flow of the third liquid to that of the first liquid. In practice, and as shown in the embodiment of FIG. 1, a third cross channel 24 is provided in the catheter body between channels 14 and 15. This third channel is shown in FIGS. 1 and 6 to be located in alignment with channel 23. Other possible locations are upstream of the second cross channel 23 as shown with dotted lines in FIG. 1 at 24a, and downstream of the second cross channel 23 as shown with dotted lines in FIG. 1 at 26b. It is preferred, however, to provide channel 24 in alignment with channel 23, since this location is believed to be the simplest to accomplish by making the channel through channel 23. This may be done after channel 23 is formed, or these channels may be simultaneously formed.

Of course, adding a further flow results in a dilution of the liquid normally running in the return channel, but, if the flow of the second liquid (volume/time unit) in relation to the flow of the first liquid is known, the dilution ratio can easily be determined. Typically, and as preferred, if the original flow rate in channel 14 is equal to that in channel 15, the resulting flow rate in channel 14 after the junction with channel 15 will be doubled and the dilution will be 1:2. Consequently, by the simple measure of adding a second flow to the return flow, it has been possible to half the time for obtaining an analysis result. The analysis apparatus may easily be set to take any dilution into consideration when computing a true analysis result. Likewise, it is possible to adjust the analysis apparatus to compensate for possible increase in return flow resistance due to the increased flow.

In the description given above, it has been implied that the flow of the second liquid in channel 15 is continuous, which leads to a certain dilution if the two liquids are mixable. It is also contemplated, however, to introduce the second liquid intermittently so as to create a 'plug' of sample followed by a 'plug' of the second liquid like a pulse train. In such case, it would be suitable if the second liquid was not mixable with the first liquid containing the sample, thus creating an undiluted sample. The second liquid may have a color or other property different from that of the first liquid with samples so as to enable optic detection of the second fluid for purposes of starting and stopping analysis or the like.

The invention being thus described, it will be obvious that the same may be varied in many ways. Such variations are not to be regarded as departure from the spirit and scope of the invention, and all such modifications as would be obvious to one skilled in the art were intended to be included within the scope of the following claims.

We claim:

1. A microdialysis probe and catheter arrangement comprising:

a catheter carrying in a distal end thereof a probe to be inserted in the body of a living being, said catheter having an elongate catheter body including a first channel for supplying a first fluid and a second channel for returning said first fluid, said first and second channels extending internally within said catheter body from a proximal end thereof to at least said probe, said probe including a microdialysis membrane defining a dialysis chamber communicating with said first and second channels, wherein a third channel extends internally within said catheter body from a proximal end thereof to at least said probe and communicates with said second channel at a point adjacent to a distal end of the microdialysis chamber in order to supply a second fluid to said second channel.

2. The microdialysis probe and catheter arrangement according to claim 1, wherein said first and second channels communicate with said microdialysis chamber by means of a first and a second cross channel, respectively, extending through said catheter body from the respective first and second channel to its exterior wall.

3. The microdialysis probe and catheter arrangement according to claim 1, wherein said third channel communicates with said second channel by means of a third cross channel extending through said catheter body.

4. The microdialysis probe and catheter arrangement according to claim 3, wherein said second and third cross channels are aligned.

5. The microdialysis probe and catheter arrangement according to claim 3, wherein said second and third cross channels are not aligned.

6. The microdialysis probe and catheter arrangement according to claim 1 wherein the first channel, the second channel, and the third channel are arranged inside the catheter body along a common diametrical plane.

7. The microdialysis probe and catheter arrangement according to claim 1, wherein the first channel, the second channel, and the third channel have equal, circular cross sections.

8. The microdialysis probe and catheter arrangement according to claim 1, wherein the microdialysis chamber surrounds an exterior wall of the catheter body, and the first channel, the second channel, and the third channel which extend parallel to each other within the catheter body.

9. A method of performing a microdialysis process, comprising the steps of:

feeding a first liquid from a proximal end of a catheter through a first channel extending internally along said catheter;

introducing said first liquid into a microdialysis chamber provided at a distal end of said catheter;

returning said first liquid together with samples collected in said microdialysis chamber to said proximal end through a second channel extending internally along said catheter;

directing a flow of a second liquid from a third channel extending internally along said catheter into said second channel to increase the flow rate therein, the second channel and the third channel each being formed inside a body of the catheter and extending from a proximal end to a distal end thereof, and communicating with each other at a point adjacent to a distal end of the microdialysis chamber.

10. The method according to claim 9, wherein said second liquid is continuously directed into said second channel.

11. The method according to claim 9, wherein said second liquid is intermittently directed into said second channel.

12. The method according to claim 9, returning said first liquid together with the samples collected in said microdialysis chamber through said second channel which communicates with the microdialysis chamber via a cross channel opening to the distal end of the microdialysis chamber.

* * * * *